(12) United States Patent
Klingler

(10) Patent No.: US 6,870,606 B2
(45) Date of Patent: Mar. 22, 2005

(54) PROCESS FOR MEASURING THE SURFACE OF A POLISHED PRECIOUS STONE

(75) Inventor: Peter Klingler, Schwaz (AT)

(73) Assignee: D. Swarovski & Co., Wattens (AT)

(*) Notice: Subject to any disclaimer, the term of this patent is extended or adjusted under 35 U.S.C. 154(b) by 305 days.

(21) Appl. No.: 10/301,738

(22) Filed: Nov. 22, 2002

(65) Prior Publication Data

US 2003/0107722 A1 Jun. 12, 2003

(30) Foreign Application Priority Data

Dec. 12, 2001 (AT) .................................. A 1942/2001

(51) Int. Cl.$^7$ .......................... G01N 21/87; G01B 11/24
(52) U.S. Cl. .......................... 356/30; 356/601; 356/613
(58) Field of Search .......................... 356/30, 601, 613

(56) References Cited

U.S. PATENT DOCUMENTS

| 4,529,305 A | * | 7/1985 | Welford et al. ............... 356/30 |
| 5,076,698 A | * | 12/1991 | Smith et al. .................. 356/30 |
| 6,567,156 B1 | * | 5/2003 | Kerner ......................... 356/30 |

* cited by examiner

*Primary Examiner*—F. L. Evans
(74) *Attorney, Agent, or Firm*—Wenderoth, Lind & Ponack, L.L.P.

(57) ABSTRACT

Process for the measurement of the surface of a polished precious stone, wherein firstly the position of at least some of the flat facet surfaces of the stone is measured in space, in particular by rotating the stone in front of a light source and examination of the shadow cast by the stone, and the facet surface is then observed under direct light.

6 Claims, 1 Drawing Sheet

PROCESS FOR MEASURING THE SURFACE OF A POLISHED PRECIOUS STONE

Figure 1:
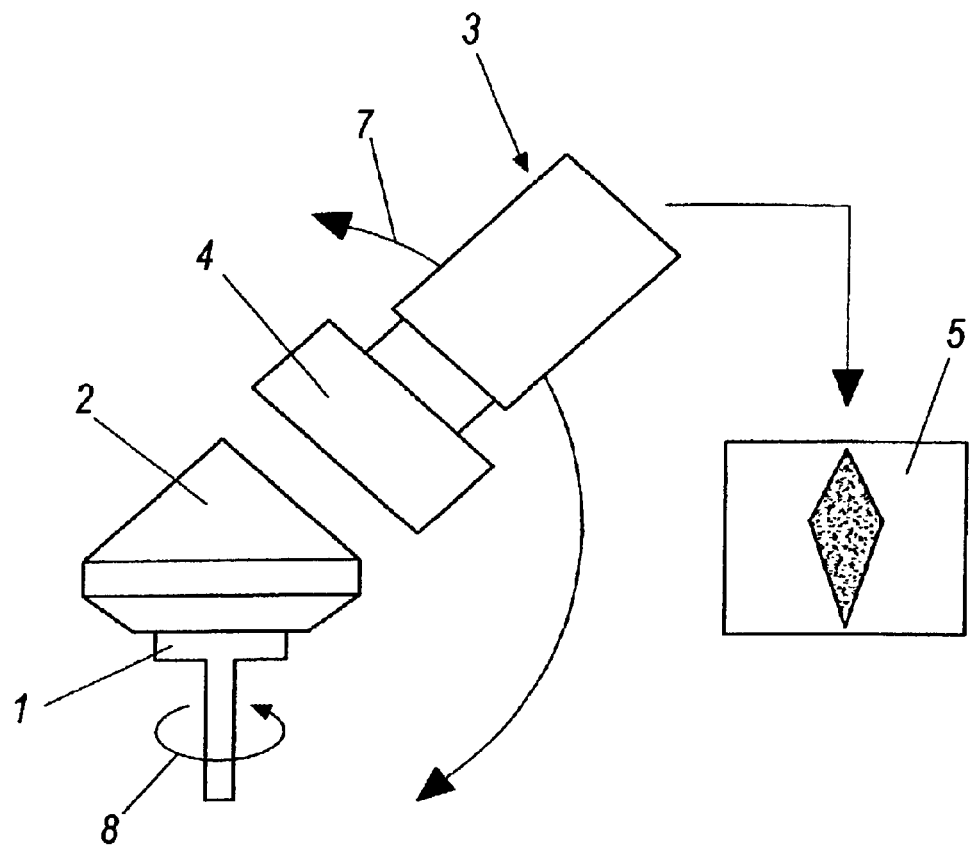

The invention relates to a process for measuring the surface of a polished precious stone, wherein firstly the position of at least some of the flat facet surfaces of the stone is measured in space, in particular by rotating the stone in front of a light source and examination of the shadow cast by the stone.

Such known processes allow a very good measurement of the flat surfaces in contact with the surface of a gem, in particular a diamond. If the stone was actually an ideal polygon of flat surfaces which meet exactly at the corner points and which are bordered by completely sharp straight edges, then the surface geometry of for example a polished diamond would already be defined. Real precious stones however differ from the ideal configuration at least insofar as they have slightly rounded edges. The distance of such edges from a straight line in which the planes adjacent to the edges meet can still be measured if need be under transmitted light. However, the transmitted-light method gives incomplete information only about where the curve of the edge begins and about how exactly several facets run together to a point.

An improvement in measuring the surface geometry in particular of diamonds would be desirable for many reasons. Firstly it would allow stones of higher quality, in particular with greater symmetry, to be produced. Furthermore, it would then be possible to graduate the polished diamond in respect of the precision of its surface shape. A more exact knowledge of the surface shape of the diamond would also be necessary in order to use existing computer programs, which calculate the brilliance of a stone from this shape, to their full advantage.

The invention improves the process defined at the outset for measuring the surface of a polished precious stone by observing the flat facet surfaces under direct light following the measurement of same in space. This proposal is not trivial insofar as the polished facets of the precious stone do not have a diffusely reflecting surface and practically rule out laser-scanning processes based on the triangulation method for the observation of the surfaces under direct light. The observation of the reflecting surfaces of a facetted precious stone is also made more difficult because not only do a large number of facets lying close together reflect the irradiated light, but internal reflections of the irradiated light also occur. If an illumination with beams falling strictly parallel to the facet normal is used to avoid this disadvantage, then as a result of the high selectivity of collimated illumination only the facet region running normally to the direction of the light appear bright in a camera with a telecentric lens.

Telecentric lenses with illumination reflected in parallel to the axis belong per se to the state of the art. It was not however obvious to use such devices for the systematic measurement of the surfaces of polished diamonds. If the camera is not in fact located from the outset in the correct orientation to the numerous facets of the stone, it receives no further evaluatable signals even with deviations on the scale of 1°. Even if the transmitted-light method itself allows the camera to be orientated precisely on the individual facets, it was surprising that by additional observation under direct light so much more information about the contour of the individual facets can be obtained that the additional expenditure is worthwhile. Through the use of a telecentric lens it is also possible to ascertain precisely the absolute dimensions of the facets.

Figure 2:
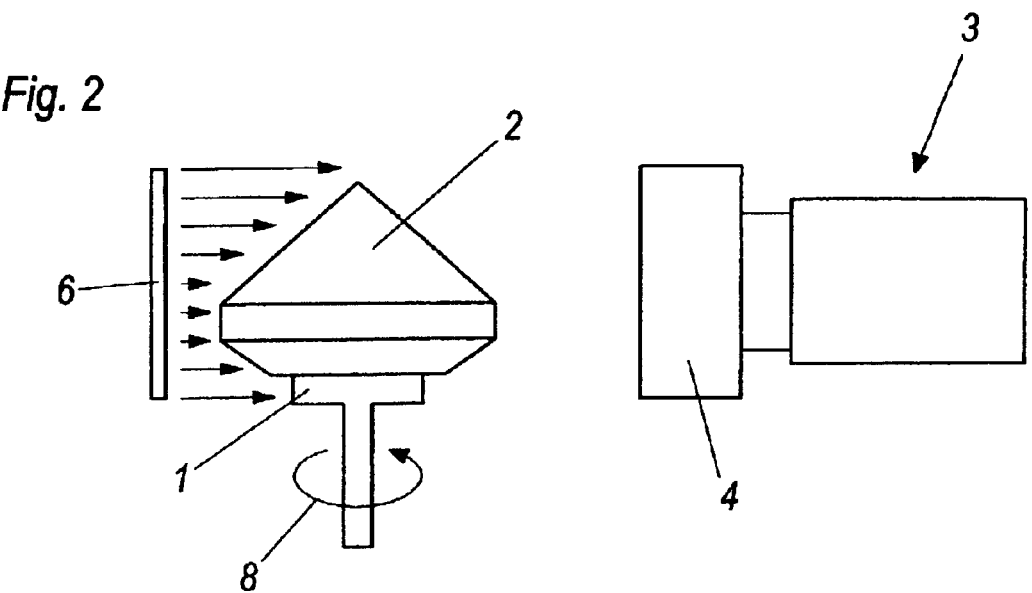

Details of the invention are explained in the following using the drawing, in which there are shown in
FIG. 1 the observation of the facets under direct light and
FIG. 2 the observation under transmitted light.

The essential part of the device shown in FIG. 1 is a camera 3 which is rotatably arranged in the focal plane in the direction of the arrow 7. The camera is to be directed normally in each case towards one of the facets of the precious stone 2, which is attached to a turntable 1 in customary manner (wax, vacuum). Each facet of the stone 2 can be aligned normally to the camera 3 by rotating the table 1 in the direction of the arrow 8 and by rotating the camera 3 in the direction of the arrow 7. In principle the illumination of the precious stone 2 takes place as a result of light reflected into the camera 3 parallel to the axis and the observation of the facet through a telecentric lens 4. The coaxial illumination can be incorporated into the lens or coupled externally, via a beam-splitter, into the lens beam path. The resulting image 5 first gives a representation of the facet in its real size, which is then enlarged.

As an alternative to the representation in FIG. 1, the camera can remain fixed in its position and the precious stone, together with the turntable, can also be rotated about a horizontal axis. This has advantages in terms of construction and control engineering, as the heavy lens no longer has to be moved.

The essence of telecentric lens systems with reflected telecentric illumination is that illumination axes and lens axes run strictly parallel. For this purpose, the high-precision front-lens of the lens, among others, is also used for the generation of the illumination beam path. In the present case, under direct light, the camera is directed normally towards the reflecting facet to be examined. The beams emerging from the lens system are therefore deflected back with a facet angle of incidence of 0° from same and subjected to imaging.

The illumination beam should be slightly diffused which is the case in practice anyway. If the camera does not stand at exactly 90° to the relevant facet due to a minimal positioning error, but deviates from it by an angle w, then a diffusivity of 2w is to be guaranteed for the illumination. The projection error produced as a result of a slight angled positioning is small.

Telecentric lenses, like entocentric lenses, have an optimum focal plane. This is due to their anallactic aperture with finite diameter so that light beams instead of light rays are involved. Telecentric lenses however have a larger depth of sharp focus zone than comparable entocentric lenses.

High-precision, two-sided telecentric lenses are now available on the market. These are telecentric in terms of lenses and imaging. The image of the edge remains symmetrical during defocussing so that sub-pixel-precision measurement of the edge position is possible. The edge position ascertained from the image thus corresponds essentially to the geometric edge position.

Under transmitted light the telecentric arrangement achieves for the invention a constant imaging scale within its telecentric region, so that the object contour is precisely represented despite variations in its object distance.

If the regions to be measured of the test piece all lie in the telecentric region of the lens system, the adjustment of the camera along its axis can then be avoided.

In principle, the represented camera could be replaced by an imaging interferometer for direct light measurement. Essential for the process is the observation of the individual facets in the direction of the surface normals without interference from light generated by other facets or by internal reflection.

So that such an observation of a precious stone, which is only a few mm in diameter and has for example 70 facets, is possible, the position of these facets must be precisely known. For a very regular stone this can be obtained through the known geometry of the stone. In practice, the systematic adjustment of the camera 3 towards the different facets of a precious stone 2 is only justified in terms of labour if the position of the facets is measured by the device in which the measurement of the facets takes place. For this purpose the camera 3 can be rotated into the position according to FIG. 2 and the stone observed in the light of the parallel bundle of rays, which comes from the light source 6. When using a retroreflector the light reflected into the camera 3 can also be used to measure the orientation of the facets of the precious stone 2 in the transmitted-light process according to FIG. 2. Precise results can be obtained if a separate light source 6 is used.

A particular advantage of the process according to the invention is that small deviations of the facets from the ideal shape, for example polishing flaws and scratches, appear realistic in the image 5. For the identification of individual stones (fingerprinting) therefore, object-type reflection patterns which are unclear and therefore can only be compared with others with difficulty, need no longer be relied upon.

Following the process according to the invention, inclusions inside the object can also be ascertained by adjusting the observation lens under direct light just far enough so that a facet no longer reflects. One can then see into the object via this facet almost without refraction of light. As a result of an additional dark-field illumination or a larger illumination aperture, internal interference is to be seen. If this is carried out in each facet, it yields sufficient information about the presence of an inclusion inside the stone.

What is claimed is:

1. Process for the measurement of the surface of a polished precious stone, wherein firstly the position of at least some of the flat facet surfaces of the stone is measured in space, in particular by rotating the stone in front of a light source and examination of the shadow cast by the stone, characterized in that the facet surfaces are then observed under direct light.

2. Process according to claim 1, characterized in that the observation under direct light takes place using a telecentric lens with a mirror effecting illumination in parallel to the axis.

3. Device for carrying out the process according to claim 1, characterized in that it includes a turntable (1) for rotating a precious stone (2) and also a camera (3) rotatable about an axis normal to the axis of the turntable with telecentric lens (4) and illumination axis-parallel thereto.

4. Device for carrying out the process according to claim 1, characterized in that it includes a holder for a precious stone rotatable about two axes running at right angles to each other and a camera with telecentric lens and illumination axis-parallel thereto.

5. Device for carrying out the process according to claim 2, characterized in that it includes a turntable (1) for rotating a precious stone (2) and also a camera (3) rotatable about an axis normal to the axis of the turntable with telecentric lens (4) and illumination axis-parallel thereto.

6. Device for carrying out the process according to claim 2, characterized in that it includes a holder for a precious atone rotatable about two axes running at right angles to each other and a camera with telecentric lens and illumination axis-parallel thereto.

* * * * *